(12) United States Patent
Habeck et al.

(10) Patent No.: US 6,278,025 B1
(45) Date of Patent: Aug. 21, 2001

(54) PROCESS FOR THE PREPARATION OF SUBSTITUTED DIBENZOYLMETHANE COMPOUNDS

(75) Inventors: Thorsten Habeck, Meckenheim; Frank Prechtl, Frankfurt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/416,894

(22) Filed: Oct. 13, 1999

(30) Foreign Application Priority Data

Oct. 16, 1998 (DE) ............................................ 198 47 778

(51) Int. Cl.$^7$ .......................... C07C 49/76; C07D 303/00
(52) U.S. Cl. .......................... 568/334; 568/313; 568/327; 568/331; 549/512
(58) Field of Search ................................. 568/308, 309, 568/334, 313, 316, 323, 325, 327, 331; 549/512, 513, 518

(56) References Cited

U.S. PATENT DOCUMENTS

| 4,387,089 | 6/1983 | De Polo | 424/59 |
| 4,489,057 | 12/1984 | Welters et al. | 424/47 |
| 5,955,496 | * 9/1999 | Hammock et al. | 514/473 |

FOREIGN PATENT DOCUMENTS

| 24 44 180 | 4/1977 | (DE) . |
| 2945125 | 7/1984 | (DE) . |
| 2-17849 | 7/1990 | (JP) . |

OTHER PUBLICATIONS

*Organikum*, 1981, 563–71.
*Ind. J. Chem.*, Sec. B, 33, 1994, 455–59.
*Angew. Chem. Int. Ed.*, 1984, 23, 847.
S. Bodforss, "Einige Keton–Kondensationreaktionen", Chemische Berichte, vol. 52, (1919) pp. 142–145.
R. Lutz et al. "Antimarlarials alpha, beta–Dimorpholinyl ketones and related compounds", Journal of Organic Chemistry, vol. 14 (1949) pp. 982–1000.
C. Weygand et al. "Zur chemischen Morphologie in homologen Reihen", Chemische Berichte, vol. 68 (1935) pp. 1825–1838.
L.V. Moiseeva et al. "Epoxidation of p'–substituted benzylideneacetiphenones", Chemical Abstracts, vol. 80, No. 23 (Jun. 10, 1974) abstract No. 132436.
J. American Chemical Society, Bd. 71, (1949) p. 3570.
Justus Liebigs Ann. Chem, Bd. 449 (1926), p. 62.

(List continued on next page.)

*Primary Examiner*—Sreeni Padmanabhan
(74) *Attorney, Agent, or Firm*—Keil & Weinkauf

(57) ABSTRACT

The invention relates to a process for the preparation of substituted dibenzoylmethane compounds of the formula I,

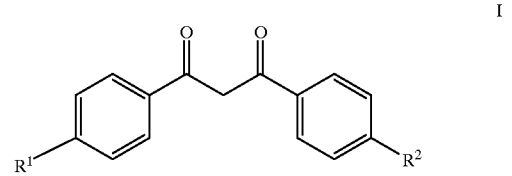

which comprises a$_1$) condensing benzaldehydes of the formula II with acetophenones of the formula III to give the chalkones of the formula IV

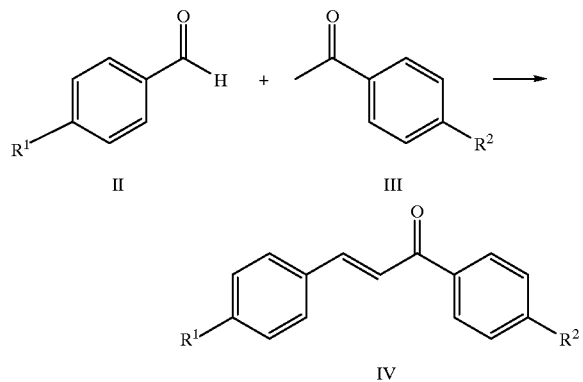

or a$_2$) condensing benzaldehydes of the formula V with acetophenones of the formula VI to give the chalkones of the formula VII

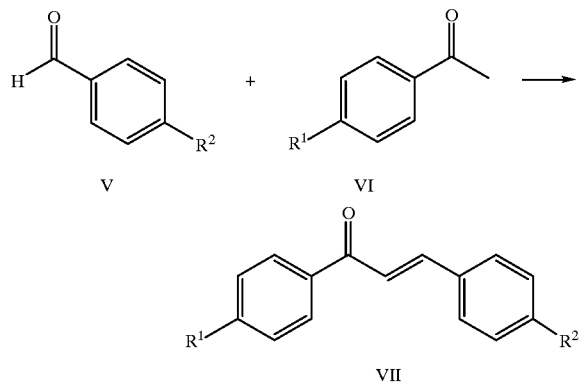

b) converting the chalcones of the formulae IV and VII into the dibenzoylmethane compounds of the formula I, the substituents R$^1$ and R$^2$ being defined as in the description.

13 Claims, No Drawings

OTHER PUBLICATIONS

V.G. Sadilkar et al., "Claisen–Schmidt reaction in a hydrotropic medium" J. Chem. Techno. Biotechnol. vol. 64 No. 4 (1995) pp. 405–410.

Chem. Ber., Bd 49, (1916), p. 2798.

K. Bowden et al. "Structure–activity relations. Part 5. Antibacterial activity of a series of substituted (E)–3–(4–phenylbenzoyl)acrylic acids,–chalcones,–2–hydroxychalcones and –alpha. –bromochalcones; addition of cysteine to substiture 3–benzoylacrylic acids and related compounds" J. Chem Rs. Synop. (1990) pp. 2801–2830.

S.S. Gill et al. "Radiometric assays for mammalian epoxide hydrolases and glutathione S–transferase" Anal. Biochem. vol. 131 No. 1 (1983).

C. Morisseau et al. "Mechanism of mammalian soluble epoxide hydrolase inhibition by chalcone oxide derivatives" Arch. Biochem. Biophys. vol. 356 No. 2, (1998) pp.214–228.

M. Suzuki et al. "Palladium(0)–catalyzed reaction of .alpha., .beta. –epoxy ketones leading to .beta.–diketones", J. Am. Chem. Soc. vol. 102, No. 6, (1980) pp. 2095–2096.

E. Hasagawa et al."Exploratory study on photoinduced single electon transfer reactions of .alpha., .beta. –epoxy ketones with amines" J. Org. Chem. vol. 56 No. 4 (1991) pp. 1631–1635.

\* cited by examiner

PROCESS FOR THE PREPARATION OF SUBSTITUTED DIBENZOYLMETHANE COMPOUNDS

The invention relates to a process for the preparation of substituted dibenzoylmethane compounds.

Sunlight which reaches the earth's surface contains UV-B radiation (280 to 320 nm) and UV-A radiation (>320 nm), which directly border the visible light region. The effect on human skin is noticeable, particularly in the case of UV-B radiation, from sunburn. Accordingly, the industry offers a relatively large number of substances which absorb UV-B radiation and thus prevent sunburn.

Dermatological investigations have shown that UV-A radiation is also perfectly capable of causing skin damage and triggering allergies by, for example, damaging the keratin or elastin. As a result, the skin's elasticity and its ability to store water are reduced, i.e. the skin becomes less supple and tends toward wrinkle formation. The remarkably high incidence of skin cancer in regions where solar irradiation is high indicates that damage to the genetic information in cells is also evidently caused by sunlight, specifically by UV-A radiation. For these reasons, the development of more efficient filter substances for the UV-A and UV-B region would therefore appear necessary.

Substances which have a dibenzoylmethane group as a structural element

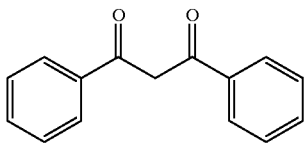

are notable for very high absorption properties in the UV-A region. Customary light protection filter substances from this class of compound are, for example, Eusolex® 8020 (INCI name: Isopropyldibenzoylmethane, Merck) and Parsol® 1789 (INCI name: Butylmethoxydibenzoylmethane, Givaudan).

DE-A-2945125 describes a process for the preparation of Parsol® 1789 by ester condensation of methyl 4-tert-butylbenzoate with 4-acetylanisole.

Because of the continually increasing demand for light protection agents which have a dibenzoylmethane group as structural element, the object was to provide a process for the preparation of substituted dibenzoylmethane compounds which is easy to carry out and affords economic advantages as a result of high yields.

This object has been achieved by a process for the preparation of substituted dibenzoylmethane compounds of the formula I,

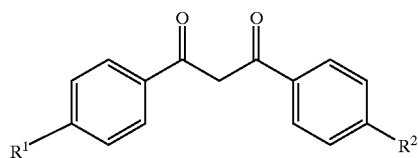

I where the substituents $R^1$ and $R^2$ independently of one another are defined as follows:

$R^1$ is $C_3-C_{12}$-alkyl;
$R^2$ is hydrogen, $C_3-C_{12}$-alkyl, $C_1-C_{12}$-alkoxy, which comprises a$_1$) condensing benzaldehydes of the formula II with acetophenones of the formula III to give the chalcones of the formula IV, in which the exocyclic double bond is in the E- or Z-configuration or a mixture thereof, and the substituents $R^1$ and $R^2$ are as defined above,

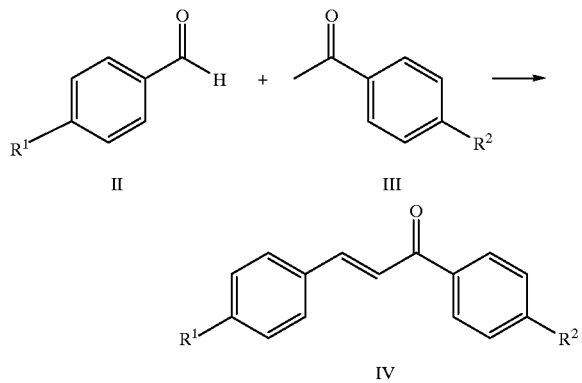

or a$_2$) condensing benzaldehydes of the formula V with acetophenones of the formula VI to give the chalcones of the formula VII, in which the exocyclic double bond is in the E- or Z-configuration or a mixture thereof, and the substituents $R^1$ and $R^2$ are as defined above, and

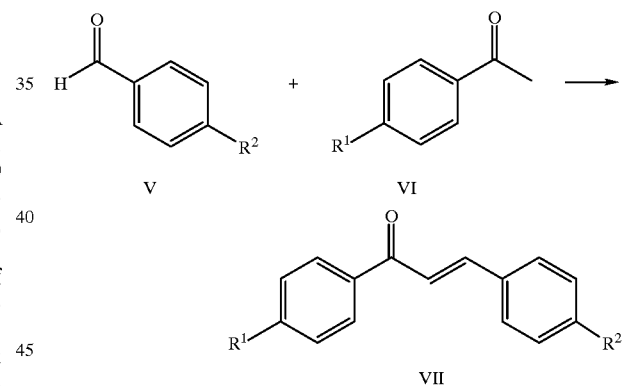

b) converting the chalcones of the formulae IV or VII into the dibenzoylmethane compounds of the formula I.

Examples of alkyl radicals $R^1$ and $R^2$ are branched or unbranched $C_3-C_{12}$ alkyl chains, preferably n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl and n-dodecyl.

Particularly preferred alkyl radicals $R^1$ and $R^2$ from the abovementioned group are the $C_3-C_6$-alkyl chains, very particularly preferably the $C_3-C_4$-alkyl chains, such as n-propyl, 1-methylethyl, n-butyl, 1-methylpropyl, 2-methylpropyl and 1,1-dimethylethyl.

Suitable alkoxy radicals $R^2$ are those having from 1 to 12 carbon atoms, preferably from 1 to 8 carbon atoms.

Examples thereof are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Particularly preferred alkoxy radicals $R^2$ are those having from 1 to 6 carbon atoms, very particularly preferably those having from 1 to 4 carbon atoms, such as methoxy, ethoxy, isopropoxy, n-propoxy, 1-methylpropoxy and n-butoxy.

The reaction of the benzaldehydes II or V with the acetophenone derivatives III or VI respectively in process steps $a_1$) or $a_2$) is carried out in accordance with aldol condensations known from the literature (see in this connection: Organikum [Organic Chemistry], VEB Deutscher Verlag der Wissenschaften, Berlin 1981, pages 563–571; Indian J. Chem. Sec. B, 33, 1994, 455–459).

The condensation can either be base- or acid-catalysed. Suitable catalysts are:

basic alkali metal and alkaline earth metal salts, preferably those which are soluble neither in the starting materials nor in the products and which can be readily removed after the reaction has finished, particularly preferably: sodium, potassium or calcium carbonate or sodium bicarbonate;

alkali metal hydroxides, preferably sodium or potassium hydroxide;

alkaline earth metal oxides, preferably calcium or magnesium oxide;

basic zeolites;

alkali metal alkoxides, for example sodium methoxide, sodium ethoxide, butyllithium;

tertiary amines, for example pyridine, morpholine, triethylamine, triethanolamine;

$NH_3$, $NaNH_2$, $NH_4OAc$;

basic aluminum oxide, basic ion exchanger;

acid catalysts, for example HCl, $H_2SO_4$, $HNO_3$, phosphoric acid, glacial acetic acid;

acid ion exchanger, for example Lewatit® S100 (Bayer).

The amount of catalysts is generally from 1 to 80 mol %, preferably from 5 to 50 mol %, based on the amount of aldehyde used.

The process is preferably carried out at temperatures from 10 to 150° C., particularly from 20 to 100° C., particularly preferably from 25 to 60° C. Specific conditions as regards the pressure are not necessary; the reaction is generally carried out at atmospheric pressure.

Solvents which can be used are alcohols, for example methanol, ethanol, propanol, isopropanol, n-butanol or isobutanol; aromatics, for example toluene or xylene; hydrocarbons, for example heptane or hexane; chlorinated hydrocarbons, for example chloroform or dichloromethane; miglyol or tetrahydrofuran. The reaction can, however, also be carried out without solvent.

The reaction can either be carried out batchwise or continuously. A continuous procedure preferably involves passing the reactant over a solid bed of an insoluble base, for example basic zeolites.

The further reaction of the chalcones IV or VII to give the dibenzoylmethane compound of the formula I in process step b) comprises $b_1$) converting the chalcones IV or VII into the compounds of the formulae VIII or IX by addition of halogens or hypohalites,

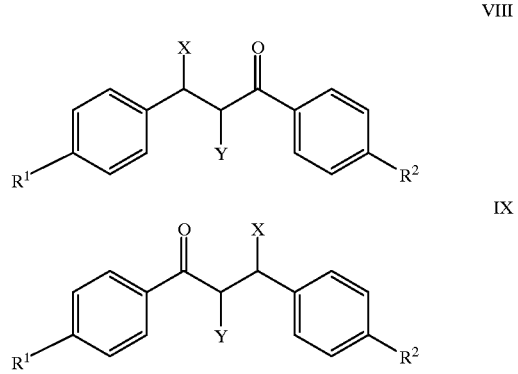

where $R^1$ and $R^2$ are as defined above, and X is halogen and OH, and Y is a halogen, and $b_2$) preparing the dibenzoylmethane compounds of the formula I from the compounds VIII and IX by elimination of HY and with or without subsequent hydrolysis.

The halogens used for the addition to the exocyclic double bond of the chalcones IV and VII are preferably bromine or chlorine, very particularly preferably chlorine. The reaction is carried out in a simple manner by mixing the two starting materials in an inert solvent. The reaction products formed are dihalogen compounds of the formulae VIII or IX in which the substituents X and Y are both bromine or chlorine, preferably chlorine.

Suitable solvents include: aliphatic and aromatic hydrocarbons, such as cyclohexane, benzene, toluene or xylene; halogenated aliphatic and aromatic hydrocarbons, such as tetrachloromethane, dichloromethane or chlorobenzene. It is, however, also possible to carry out the halogen addition in alcohols such as, for example, ethanol or propanol.

The reaction temperatures are in the range from −10° C. to 150° C., preferably in the range from 0° C. to 80° C., particularly preferably in the range from 5° C. to 50° C., very particularly preferably in the range from 10° C. to 30° C.

The use of hypohalites, such as sodium hypochlorite or sodium hypobromite, instead of the halogens gives the corresponding halohydrins of the formulae VIII or IX, where X is OH and Y is halogen, preferably bromine or chlorine, particularly preferably chlorine.

Known base-catalysed elimination of HY, in particular HBr or HCl, can be used to convert the abovementioned halohydrins into the desired dibenzoylmethane compounds of the formula I.

In the case of the dihalides VIII or IX (X=Y=Br or Cl), the elimination of HY is followed by base-catalysed hydrolysis, for example, in the presence of alkali alkoxides, such as sodium methoxide, at temperatures between 20 and 100° C., preferably between 30 and 95° C., particularly preferably between and 90° C., which leads to the desired dibenzoylmethane compounds of the formula I.

Another method of preparing, in process step b), the dibenzoylmethane compounds I from the chalcones IV and VII comprises b₁) converting the chalcones IV or VII into the oxiranes of the formulae VIIIa or IXa by epoxidation,

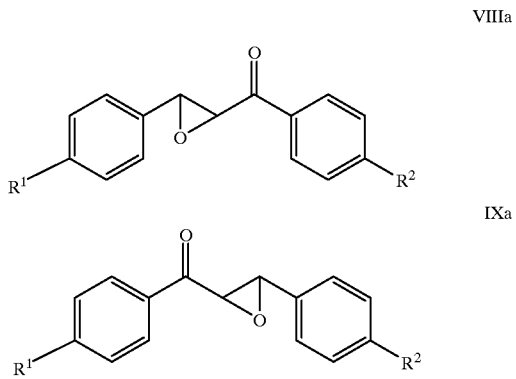

VIIIa

IXa and b₂) preparing the dibenzoylmethane compounds of the formula I from the epoxides by ring opening.

The epoxidation of the chalcones IV and VII can inter alia be carried out in a manner known per se in the presence of hydrogen peroxide/NaOH in the pH range from 8 to 13, in the presence of peroxy acids, such as peroxybenzoic acid or m-chloroperoxybenzoic acid, in the presence of dioxiranes, such as dimethyldioxirane, in the presence of hydroperoxides, such as tert-butyl hydroperoxide, or in the presence of inorganic persulfates, such as potassium hydrogen persulfate.

The reaction is generally carried out in aqueous-alcoholic solvents at temperatures from −20° C. to 150° C., preferably from −10° C. to 80° C., particularly preferably from 0° C. to 60° C., very particularly preferably from 0° C. to 30° C.

The opening of the oxirane ring can be carried out in the presence of transition metal complexes, such as tetrakistriphenylphosphinepalladium and is described inter alia by Noyori et al., Angew. Chem. Int. Ed., 1984, 23, 847.

The novel process is notable for the fact that the dibenzoylmethane compounds of the formula I prepared therewith can be obtained in high yields and in a technically simple manner.

In a particular embodiment of the novel process, either a₁) benzaldehydes of the formula II where $R^1$ is $C_3$–$C_4$-alkyl, in particular 4-(1,1-dimethylethyl)benzaldehyde, are reacted with acetophenone derivatives of the formula III where $R^2$ is $C_1$–$C_4$-alkoxy, in particular 4-methoxyacetophenone, to give the corresponding chalcones of the formula IV, in particular to give 4-(1,1-dimethylethyl)-benzylidene-4'-methoxyacetophenone, or a₂) benzaldehydes of the formula V where $R^2$ is $C_1$–$C_4$-alkoxy, in particular 4-methoxybenzaldehyde, are reacted with acetophenone derivatives of the formula VI where $R^1$ is $C_3$–$C_4$-alkyl, in particular 4-(1,1-dimethylethyl)acetophenone, to give the corresponding chalcones of the formula VII, in particular to give 4-methoxybenzylidene-4'-(1,1-dimethylethyl) acetophenone, the chalcones IV and VII then being converted directly and without prior isolation and purification, into the dibenzoyl methane compounds of the formula I where $R^1$ is $C_3$–$C_4$-alkyl and $R^2$ is $C_1$–$C_4$-alkoxy, in particular into 4-(1,1-dimethylethyl)-4'-methoxydibenzoylmethane by means of chloroaddition, elimination of HCl and subsequent basic hydrolysis.

The invention likewise provides chalcones of the formula IV,

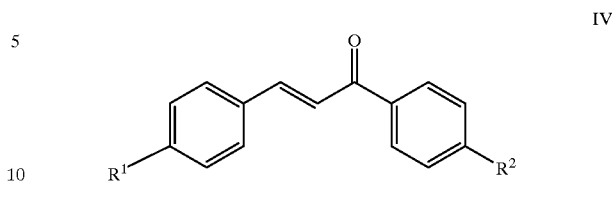

IV where the exocyclic double bond is in the E- or Z-configuration or a mixture thereof, and the substituents $R^1$ and $R^2$ independently of one another are defined as follows:

$R^1$ is $C_3$–$C_4$-alkyl;

$R^2$ is hydrogen, $C_1$–$C_4$-alkoxy.

Examples of alkyl radicals $R^1$ and $R^2$ are branched or unbranched $C_3$–$C_4$-alkyl chains, preferably n-propyl, 1-methylethyl, n-butyl, 1-methylpropyl-, 2-methylpropyl and 1,1-dimethylethyl.

Suitable alkoxy radicals $R^2$ are those having from 1 to 4 carbon atoms.

Examples thereof are:

| | |
|---|---|
| methoxy | ethoxy |
| isopropoxy | n-propoxy |
| 1-methylpropoxy | n-butoxy |

Preference is given to chalcones of the formula IV in which $R^1$ is isopropyl or 1,1-dimethylethyl, and $R^2$ is hydrogen or methoxy, in particular 4-(1,1-dimethylethyl) benzylidene-4'-methoxyacetophenone.

The invention further provides chalcones of the formula VII,

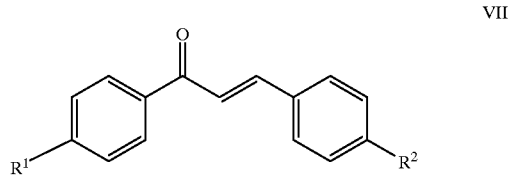

VII where the exocyclic double bond is in the E- or Z-configuration or a mixture thereof, and the substituents $R^1$ and $R^2$ independently of one another are defined as follows:

$R^1$ is $C_3$–$C_4$-alkyl;

$R^2$ is hydrogen, $C_1$–$C_4$-alkoxy.

The more precise definitions of the substituents $R^1$ and $R^2$ for the chalcones VII correspond to those of compound IV.

Preference is given to chalcones of the formula VII in which $R^1$ is isopropyl or 1,1-dimethylethyl, and $R^2$ is hydrogen or methoxy, in particular 4-methoxybenzylidene-4'-(1,1-dimethylethyl)-acetophenone.

The invention also provides diaryl compounds of the formula VIII,

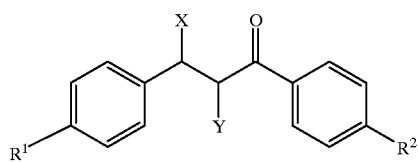

VIII where the substituents independently of one another are defined as follows:

X is halogen, OH;
Y is halogen;
$R^1$ is $C_3$–$C_{12}$-alkyl;
$R^2$ is hydrogen, $C_3$–$C_{12}$-alkyl, $C_1$–$C_{12}$-alkoxy, it also being possible for the substituents X and Y together with the carbon atoms to which they are bonded to form an oxirane ring.

Examples of halogens X and Y are, preferably, bromine and chlorine, particularly preferably chlorine.

Examples of alkyl radicals $R^1$ and $R^2$ are branched or unbranched $C_3$–$C_{12}$-alkyl chains, preferably n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl and n-dodecyl.

Particularly preferred alkyl radicals $R^1$ and $R^2$ from the abovementioned group are the $C_3$–$C_6$-alkyl chains, very particularly preferably the $C_3$–$C_4$-alkyl chains, such as n-propyl, 1-methylethyl, n-butyl, 1-methylpropyl, 2-methylpropyl and 1,1-dimethylethyl.

Suitable alkoxy radicals $R^2$ are those having from 1 to 12 carbon atoms, preferably having 1 to 8 carbon atoms.

Examples thereof are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Particularly preferred alkoxy radicals $R^2$ are those having from 1 to 6 carbon atoms, very particularly preferably those having from 1 to 4 carbon atoms, such as methoxy, ethoxy, isopropoxy, n-propoxy, 1-methylpropoxy and n-butoxy.

If the substituents X and Y form an oxirane ring together with the carbon atoms to which they are bonded, compounds of the following structure VIIIa arise.

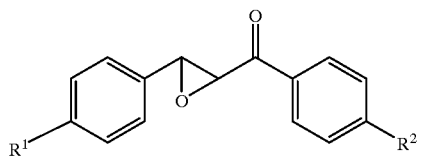

VIIIa

Preference is given to diaryl compounds of the formula VIII where X and Y are OH, Br, Cl or an oxirane ring formed together with the carbon atoms to which they are bonded, $R^1$ is $C_3$–$C_6$-alkyl and $R^2$ is hydrogen, $C_3$–$C_6$-alkyl or $C_1$–$C_6$-alkoxy.

Particular preference is given to diaryl compounds of the formula VIII where X and Y are Cl or an oxirane ring formed together with the carbon atoms to which they are bonded, $R^1$ is $C_3$–$C_6$-alkyl and $R^2$ is hydrogen or $C_1$–$C_6$-alkoxy.

Very particular preference is given to diaryl compounds of the formula VIII where X and Y are Cl or, jointly, are an oxirane ring formed together with the carbon atoms to which they are bonded, $R^1$ is $C_3$–$C_4$-alkyl, in particular 1,1-dimethylethyl, and $R^2$ is $C_1$–$C_4$-alkoxy, in particular methoxy.

The invention also provides diaryl compounds of the formula IX,

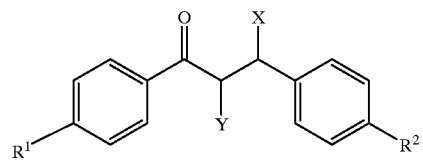

IX where the substituents independently of one another are defined as follows:

X is halogen, OH;
Y is halogen;
$R^1$ is $C_3$–$C_{12}$-alkyl;
$R^2$ is hydrogen, $C_3$–$C_{12}$-alkyl, $C_1$–$C_{12}$-alkoxy, it also being possible for the substituents X and Y to form an oxirane ring together with the carbon atoms to which they are bonded as in formula IXa.

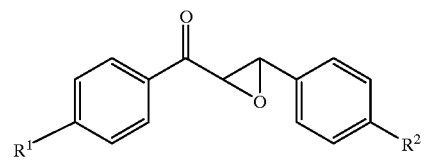

IXa

The more precise definitions of the substituents $R^1$ and $R^2$ and X and Y of compound IX correspond to those of compound VIII.

Preference is given to diaryl compounds of the formula IX, where X and Y are OH, Br, Cl or an oxirane ring formed together with the carbon atoms to which they are bonded, $R^1$ is $C_3$–$C_6$-alkyl and $R^2$ is hydrogen, $C_3$–$C_6$-alkyl or $C_1$–$C_6$-alkoxy.

Particular preference is given to diaryl compounds of the formula IX where X and Y are Cl or an oxirane ring formed together with the carbon atoms to which they are bonded, $R^1$ is $C_3$–$C_6$-alkyl and $R^2$ is hydrogen or $C_1$–$C_6$-alkoxy.

Very particular preference is given to diaryl compounds of the formula IX where X and Y are Cl or, jointly, are an oxirane ring formed together with the carbon atoms to which they are bonded, $R^1$ is $C_3$–$C_4$-alkyl, in particular 1,1-dimethylethyl, and $R^2$ is $C_1$–$C_4$-alkoxy, in particular methoxy.

The examples below serve to illustrate the novel process in more detail.

EXAMPLE 1

Preparation of 4-(1,1-dimethylethyl)benzylidene-4'-methoxyacetophenone 97.6 g (0.65 mol) of 4-methoxyacetophenone and 105.4 g (0.65 mol) of 4-(1,1-dimethylethyl)benzaldehyde were dissolved in 600 ml of methanol in a 1 1 round-bottom flask fitted with internal thermometer, reflux condenser and paddle stirrer. 20 g (0.05 mol) of 10% NaOH were then added at room temperature. The mixture was then stirred at 30° C. The crystals which formed were filtered off, washed with 50 ml of cold methanol and then dried under reduced pressure (150 mbar) at 75° C. Yield: 172 g (90% yield) of pale yellow crystals; m.p.: 114–116° C.; purity: >99%.

EXAMPLE 2

Preparation of 4-(1,1-dimethylethyl)-4'-methoxydibenzoylmethane 7.35 g (0.025 mol) of 4-(1,1-dimethylethyl)benzylidene-4'-methoxyacetophenone from Example 1 were suspended in 50 ml of xylene and reacted with 2 g (0.028 mol) of chlorine gas at from 0 to 5° C. over the course of 1 h. 14.5 g (0.08 mol) of a 30% strength by weight solution of sodium methoxide in methanol were added to this solution, and the mixture was heated at 80° C. for 1 h. 8.0 g of a 37% strength by weight aqueous HCl solution were then added, and then the mixture was stirred at 80° C. for 2 h. The NaCl which precipitated out was filtered off, the solvent was distilled off, and the residue was recrystallized from methanol. This gave 6.58 g of colorless crystals having a purity of >99%. The yield was 85%.

EXAMPLE 3

Preparation of 4'-methoxyphenyl-[3-{4-(1,1-dimethylethylphenyl)oxiranyl}]methanone 20.9 g (0.071 mol) of 4-(1,1-dimethylethyl)benzylidene-4'-methoxyacetophenone from Example 1 was suspended in 350 ml of EtOH, and at from 20 to 25° C., 11.5 ml of a 25% strength by weight NaOH solution were added. 9.65 g (0.085 mol) of an aqueous 30% strength by weight hydrogen peroxide solution were then added dropwise at 20° C. over the course of 10 min. and then the mixture was stirred for 1 h at this temperature. The solvent was distilled off under reduced pressure, and the residue was purified by column chromatography (SiO$_2$; cyclohexane/ethyl acetate). This gave 17.6 g (80% yield) of a yellowish oil.

EXAMPLE 4

Preparation of 4-(1,1-dimethylethyl)-4'-methoxydibenzoylmethane 40 mg (0.1 mmol) of tetrakistriphenylphosphine-palladium and 0.1 g (0.3 mmol) of ethylene-1,2-diphenylphosphine were added to 1 g (3.2 mmol) of the epoxide from Example 3, and the mixture was stirred at 140° C. for 7 h. The residue was purified by column chromatography. This gave 0.94 g of 4-(1,1-dimethylethyl)-4'-methoxydibenzoylmethane (94% yield) as colorless crystals having a purity of >99%.

We claim:

1. A process for the preparation of substituted dibenzoylmethane compounds of the formula I,

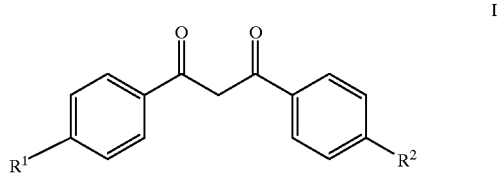

where the substituents $R^1$ and $R^2$ are defined as follows:

$R^1$ is 1,1-dimethylethyl;

$R^2$ is methoxy, which comprises a$_1$) condensing benzaldehydes of the formula II with acetophenones of the formula III to give the chalcones of the formula IV, in which the exocyclic double bond is in the E- or Z-configuration or a mixture thereof, and the substituents $R^1$ and $R^2$ are as defined above, or

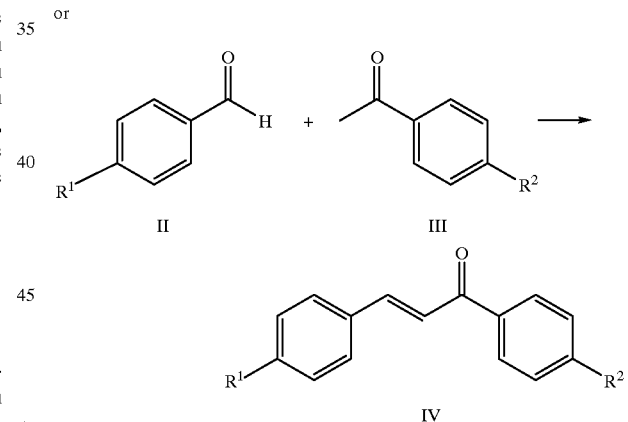

a$_2$) condensing benzaldehydes of the formula V with acetophenones of the formula VI to give the chalcones of the formula VII, in which the exocyclic double bond is in the E- or Z-configuration or a mixture thereof, and the substituents $R^1$ and $R^2$ are as defined above, and

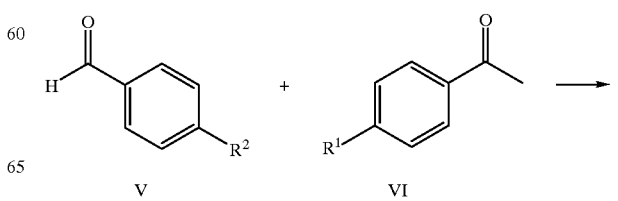

-continued

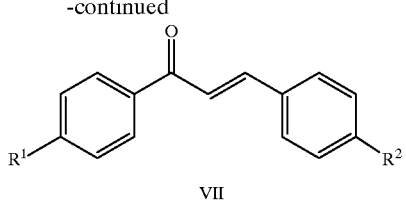

VII b) converting the chalcones of the formulae IV or VII into the dibenzoylmethane compounds of the formula I.

2. A process as claimed in claim 1, wherein the condensation in process steps $a_1$) and $a_2$) is carried out in the presence of a base.

3. A process as claimed in claim 1, wherein, in process step b), the chalcones IV or VII $b_1$) are converted into the compounds of the formulae VIII or IX by addition of halogens or hypohalites,

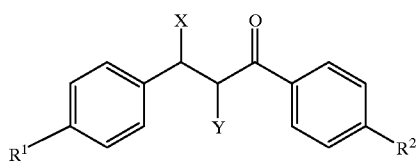

VIII

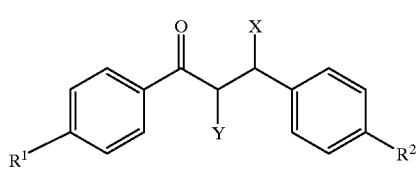

IX wherein, independently of one another, X is halogen or OH, and Y is a halogen, and $b_2$) the dibenzoylmethane compounds of the formula I are prepared from the compounds VIII and IX by elimination of HY and with or without subsequent hydrolysis.

4. A process as claimed in claim 1, wherein, in process step b), the chalcones IV or VII $b_1$) are converted into the oxiranes of the formulae VIIIa or IXa by epoxidation,

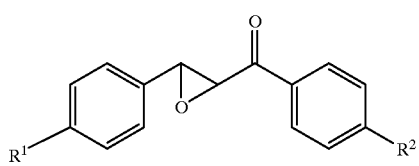

VIIIa

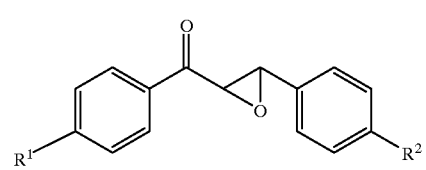

IXa and $b_2$) the dibenzoylmethane compounds of the formula I are prepared from the oxiranes VIIIa and IXa by ring opening.

5. A process as claimed in claim 1, wherein the chalcones of the formulae IV and VII prepared in the process steps $a_1$) and $a_2$) are reacted without isolation and purification to give the dibenzoylmethane compounds of the formula I.

6. A chalcone of the formula IV,

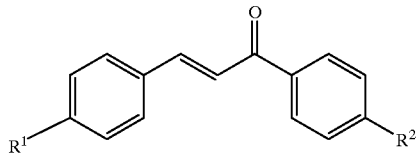

IV where the exocyclic double bond is in the E- or Z-configuration or a mixture thereof, and the substituents $R^1$ and $R^2$ are defined as follows:

$R^1$ is 1,1-dimethylethyl;

$R^2$ is methoxy.

7. A chalcone of the formula VII,

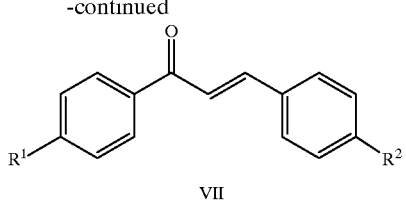

VII where the exocyclic double bond is in the E- or Z-configuration or a mixture thereof, and the substituents $R^1$ and $R^2$ are defined as follows:

$R^1$ is 1,1-dimethylethyl;

$R^2$ is methoxy.

8. A diaryl compound of the formula VIII,

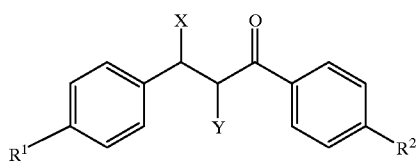

VIII where the substituents independently of one another are defined as follows:

X is halogen, OH;

Y is halogen;

$R^1$ is 1,1-dimethylethyl;

$R^2$ is methoxy, it also being possible for the substituents X and Y together with the carbon atoms to which they are bonded to form an oxirane ring.

9. A diaryl compound as claimed in claim 8, where X and Y are Cl.

10. A diaryl compound as claimed in claim 8, where X and Y are an oxirane ring formed together with the carbon atoms to which they are bonded.

11. A diaryl compound of the formula IX,

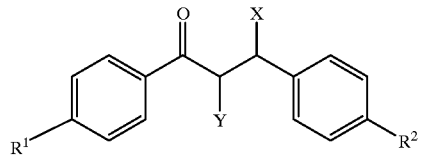

IX where the substituents independently of one another are defined as follows:

X is halogen, OH;

Y is halogen;

$R^1$ is 1,1-dimethylethyl;

$R^2$ is methoxy, it also being possible for the substituents X and Y to form an oxirane ring together with the carbon atoms to which they are bonded.

12. A diaryl compound as claimed in claim 11, where X and Y are Cl.

13. A diaryl compound as claimed in claim 11, where X and Y are an oxirane ring formed together with the carbon atoms to which they are bonded.

* * * * *